(12) United States Patent
Aimonen et al.

(10) Patent No.: US 7,317,198 B2
(45) Date of Patent: Jan. 8, 2008

(54) METHOD FOR DETERMINING THE SCALE OF AN OBSERVATION AREA

(75) Inventors: Pertti Aimonen, Pirkkala (FI); Hannes Kalaniemi, Jyvaskyla (FI); Harri Mustonen, Jyvasklya (FI)

(73) Assignee: Metso Automation Oy, Helsinki (FI)

( * ) Notice: Subject to any disclaimer, the term of this patent is extended or adjusted under 35 U.S.C. 154(b) by 180 days.

(21) Appl. No.: 10/509,043

(22) PCT Filed: Mar. 26, 2003

(86) PCT No.: PCT/FI03/00230

§ 371 (c)(1),
(2), (4) Date: Jun. 1, 2005

(87) PCT Pub. No.: WO03/081218

PCT Pub. Date: Oct. 2, 2003

(65) Prior Publication Data

US 2005/0199831 A1    Sep. 15, 2005

(30) Foreign Application Priority Data

Mar. 27, 2002  (FI) .................................. 20020584

(51) Int. Cl.
*G01N 21/86* (2006.01)

(52) U.S. Cl. ................................. 250/559.01

(58) Field of Classification Search .......... 250/559.01, 250/559.03, 559.05, 559.06, 559.07, 559.08, 250/559.1; 382/141; 700/143, 122, 127, 700/142

See application file for complete search history.

(56) References Cited

U.S. PATENT DOCUMENTS

| 4,490,617 A | 12/1984 | Loose |
| 4,491,868 A | 1/1985 | Berridge, Jr. et al. |
| 5,774,177 A * | 6/1998 | Lane ............................ 348/88 |
| 5,821,990 A | 10/1998 | Rudt et al. |
| 5,845,002 A | 12/1998 | Heck et al. |
| 6,040,853 A | 3/2000 | Delagnes et al. |

FOREIGN PATENT DOCUMENTS

| EP | 1 033 881 A2 | 9/2000 |
| EP | 1 096 777 A1 | 5/2001 |
| WO | WO 01/21516 A2 | 3/2001 |

* cited by examiner

*Primary Examiner*—David Porta
*Assistant Examiner*—Djura Malevic
(74) *Attorney, Agent, or Firm*—Oliff & Berridge, PLC.

(57) ABSTRACT

The invention relates to a method in the control of the quality or the condition of a fibre web (21) on the basis of optical imaging diagnostics, wherein the fibre web (21) under examination and/or means (22, 23) relating to the processing of the fibre web are monitored with at least one optical imaging measuring device (1 to N). According to the method, the scale of the observation area of said at least one imaging measuring device (1 to N) is calibrated, when said measuring device is taken into use, by means of one or more calibration objects placed in the observation area of the measuring device, to correct the perspective error caused by the position between said measuring device and the object (21, 22, 23) observed by it.

15 Claims, 5 Drawing Sheets

METHOD FOR DETERMINING THE SCALE OF AN OBSERVATION AREA

FIELD OF THE INVENTION

The invention relates to a method in the control of the quality or the condition of a fibre web on the basis of optical diagnostics by imaging, the control being applied in connection with the manufacturing or finishing process of a paper web.

BACKGROUND OF THE INVENTION AND PRIOR ART

There is a constant aim to increase the web speeds utilized in the manufacturing and finishing processes of paper, paperboard and other corresponding web-like materials in order to improve the production rate. When the web speeds are increased, it is, however, necessary to monitor the function and state of the process in a more detailed manner than before in order to avoid an increase in web breaks that impair the production rate and in various defects in the quality of the fibre web.

One method which has been found to be very efficient in the real-time monitoring of a rapidly moving fibre web and its path is to use optical diagnostic methods. Advantages of the optical methods include, for example, the possibility to take measurements of an object in a contactless manner and to take the measurements with a rapid time response. Several examples of applying optical methods in the manufacturing and finishing processes of web-like materials are known from prior art.

The present invention relates to optical imaging diagnostics for storing a spatially resolved visual image or other spatially resolved, optically measurable data about an object to be examined. In optical imaging systems, the detectors that are currently used are typically electrical matrix or line scan cameras, such as CCD cameras (charged coupled devices).

U.S. Pat. No. 5,821,990 discloses, on the principle level, a monitoring system in which measuring positions are arranged at different locations along the process to be monitored. In these measuring positions, the measuring devices used can be, for example, video cameras, and said monitoring system is suitable for use also in connection with a paper manufacturing process.

One example of commercially available optical systems, which are particularly suitable for the real-time monitoring of a fibre web and its path, are so-called web runnability monitoring (WRM) systems. These systems may comprise even several tens of camera units arranged to record an image of the fibre web and the machine means related to its processing at different points in the process. The primary function of WRM systems is to visually observe and analyze web breaks and the web runnability phenomena of the fibre web related therewith. The analysis is made by monitoring video sequences recorded in connection with said events in different camera positions along the path.

The basic principle of the WRM system is shown in FIG. 1. The camera units 1 to N may be placed, according to the need, at different points of the path of the fibre web, from the wet end of the paper machine all the way to the reeling up of the paper web. At present, single camera units used in the system are typically CCD cameras which operate on the visible wavelength range and which produce an analog video signal 10 to be transmitted to computers used as image processing units 11, 12 for image capturing, storage, digital image processing, and analysis. The results of the image analysis can be viewed via a user interface 13 placed in a control room, and the visual image produced by the camera units 1 to N can also be viewed in its unprocessed form in real time, if necessary, via video monitors placed in the control room.

Troubleshooting typically requires the examination of video samples recorded from different steps of the manufacturing process, i.e. recorded with the different camera units 1 to N. Video sequences corresponding to the same point of the moving fibre web but recorded in different camera positions 1 to N at different times can be used to find out which step in the process is the origin of the cause for a defect. For example, if a break caused by an edge defect or a hole in the web is detected in the reel-up of the paper machine (camera unit N in FIG. 1), one, must first determine if a web defect causing the break is already visible in an earlier step in the manufacturing process, that is, for example in images stored by camera units N-1, N-2. To determine this, the user of the monitoring system must find, from the video recordings of the camera units preceding the reel-up, the corresponding web section where the web defect that caused the break can be observed for the first time.

Naturally, it will be obvious that in practice, problems in the runnability of the paper web must be solved as quickly as possible to eliminate the cause of the disturbance as quickly as possible and thereby to prevent a decrease in the production or an impairment in the quality of the product.

Because of the quick movement of the web in the longitudinal direction, i.e. the machine direction, a defect in the web, which defect is visible for example in the reel-up at a given moment of time, occurs a few seconds earlier in the preceding steps of the process, for example in the press. Therefore, synchronization of the camera units 1 to N is used in the monitoring systems, such as WRM systems, to find, in the recordings of each camera position, the points always corresponding to the same area of the web in the longitudinal direction of the web. These problems involved in the movement of the web are discussed in Finnish patent application 990428, which presents a method for synchronizing image information from camera units monitoring a process, in the machine direction.

In addition to the longitudinal direction of the web, however, it is also very important to know the position of defects occurring in the web in the cross machine direction, to localize the defects in the paper web. After all, the width of the paper web may be even in the order of 10 metres in modern paper machines. However, in WRM systems and also other corresponding imaging systems, the determination of defects in the cross machine direction is, in practice, complicated by factors to be described below.

FIG. 2 shows, in a principle view, the placement of a single camera unit N of the WRM system in a paper machine, seen in the direction of the web 21. In FIG. 2, the web 21 travels in the direction indicated by an arrow, between rolls 22 and 23. In practice, because of the structure of the paper web and the conditions of the imaging location, the camera unit N must be typically placed outside the actual path of the web 21, as shown in FIG. 2. The camera unit N is thus trained on the web or another object to be monitored, either from the operating side of the paper machine (position 100 in FIG. 2) or from the so-called maintenance side (position 200 indicated with a broken line in FIG. 2). As a result, the image of the web 21 or another object, recorded by the camera unit N, is a perspective view, which makes it more difficult to find the the exact locations of the image area and the objects shown in said image in the cross machine direction of the web 21. In other words, the image of the camera unit N becomes a perspective representation, because the image is recorded at an imaging angle A to the cross machine direction of the paper web, the imaging angle A deviating from the direction C perpendicular to the transverse direction of the paper web.

FIG. 3 also shows the situation of FIG. 2 seen from the side. FIG. 3 shows that the imaging takes place at an imaging angle B to the longitudinal direction of the web 21, the imaging angle B being also typically different from the direction D perpendicular to the longitudinal direction of the paper web.

Now, said imaging angles A, B of the camera units in successive camera units 1 to N in the travel direction of the paper web, and also the other properties of the camera units 1 to N, such as the enlargement of the optics used in them, may vary from one imaging position to another; therefore, in practice, the imaging takes place from different perspectives and with different enlargements in the different imaging positions. This makes it significantly more difficult, in practice, to determine the imaging or monitoring area of the web 21 or other object accurately in the transverse direction, wherein it is also very difficult to determine the precise location of the phenomena visible in the image, in the transverse direction. In practice, images recorded as perspective representations must be interpreted, in the transverse direction of the web, subjectively according to the user's own assessment. In other words, the user evaluates, on the basis of his/her experience, the transverse location of the phenomena occurring in the images. Furthermore, it is obvious that the perspective may, in some situations, make the interpretation of the images more difficult also in the scale in the machine direction.

From prior art, also so-called web inspection systems (WIS) are known, whose principle of operation is disclosed more closely, for example, in the publication WO 01/21516. FIG. 4 shows, in a principle view corresponding to FIG. 2, the placement of camera units of the WIS system in the cross machine direction of the web 21.

In the WIS system, several camera units 40 are fixed in a camera beam 41 above the paper web in such a way that the imaging direction of a single camera unit 41 is substantially transverse to the web 21. By arranging the fields of vision of adjacent camera units 40 to be partly overlapping, the WIS system can be used to cover the width of the web 21 in the cross machine direction without significant perspective errors in the observation area, wherein it is now possible to record the precise location of web defects detected in the images in the cross machine direction.

In practice, however, a significant problem in the implementation of the WIS system and other corresponding systems is that, for example because of the space required by the camera beam 41 in the transverse direction of the web, the apparatus required by the system can only be installed in certain locations along the path of the paper web. Furthermore, the apparatus for a single imaging position will become relatively expensive, due to the large number of camera units 40. For these reasons, among other things, apparatuses complying with the WIS system are, in practice, typically installed in one imaging position only: at the final section of the paper machine, right before the reel-up.

In this imaging position, good measuring accuracy is achieved with the WIS system in the transverse direction of the web 21, because due to the placement of the camera units 40, the imaging takes place substantially without perspective errors. Furthermore, in said final section of the paper machine, the moisture of the web 21 is already settled, wherein no problems are, in practice, caused by the drying shrinkage in the transverse direction of the web.

It is obvious that the use of imaging systems of the WIS system type is primarily limited solely to the monitoring of the fibre web itself, because due to the size and structure of the apparatus, its placement to record images of other objects along the path is very difficult. In the wet end of the paper machine, the imaging with an apparatus complying with the WIS system, in which the camera units 40 are placed relatively close to the object to be imaged, would also be disturbed by e.g. water mist or water spraying from the paper web. Furthermore, the structure of the WIS system with the camera beam extending across the whole paper web would significantly encumber the service and maintenance work of the paper machine.

For the above-described reasons, it is thus typical that in the same paper machine, an apparatus of the WIS system, placed in one imaging position at the dry end, is used for measuring the properties of the fibre web itself, and in addition, a separate WRM system is used for monitoring the fibre web and the machine means (rolls, felts) involved in its processing, to troubleshoot web breaks and phenomena related to them.

Basic Principle and Most Important Advantages of the Invention

The primary aim of the present invention is to provide a new method for determining the scale of an observation area more precisely than before in the control of the quality or the condition of a fibre web on the basis of optical imaging diagnostics, wherein the imaging measurement is performed as perspective imaging.

A particular aim of the invention is to make it possible to compensate for a scale error caused by the perspective in visual images recorded by cameras or other spatially resolved information measured in an imaging manner, wherein it is possible to determine the precise location of phenomena occurring in the images, particularly in the transverse direction of the web.

The essential basic idea of the invention is that when an object, such as a fibre web and/or means relating to its processing, are measured in an imaging manner in such a way that the imaging direction used by the measuring means, for example a camera unit, causes a scale error due to the imaging perspective, in the visual image or other location-resolved measuring result to be recorded, said scale error can be corrected by calibrating the imaging or observation area of the measuring device when the measuring device is taken into use, or in connection with its maintenance or a corresponding event.

According to the invention, the calibration is preferably performed in such a way that when the measuring device is taken into use, calibration points are provided at the location of the object to be imaged or above it in the observation area of the measuring device, wherein the real distances between the calibration points, i.e. the dimensions of the scale formed by them, are precisely known. By means of this calibration data, the system can later correct the distortion caused by the perspective in the data to be measured by imaging, and compute the precise location of interesting objects or phenomena detected in, for example, visual images, particularly in the transverse direction of the paper web. According to the invention, the information measured by imaging is corrected and later analyzed preferably in digital format in a computer used as an image processing unit, or the like.

The invention is particularly suitable for use in combination with monitoring systems of the WRM type, using several camera units producing a visual image and placed in different imaging positions along the path of the paper web, from the wet end all the way to the reeling up. The invention allows the placement of the camera units at the side and diagonally in relation to the object to be imaged so that the camera units can be placed in locations where they are shielded and do not disturb the use or maintenance of the paper machine itself. By means of the invention, the images recorded by each camera unit can be brought to correspond precisely to each other, particularly in their scale in the transverse direction of the web, although the placement of the cameras and the other properties vary, depending on the image position.

A significant advantage of the invention is that it makes it possible, in WRM systems or the like, to temporally synchronize the camera units 1 to N, successive in the machine direction, more accurately and more easily than before. By means of the invention, it is now possible to automatically recognize, in recordings from different camera positions brought to comply with each other, a defect or another phenomenon occurring at a given point in the transverse direction of the web, and this information can be utilized further to synchronize image information from different camera units in the machine direction.

The method according to the invention can be applied for monitoring the moving web itself, or for monitoring the condition of means which are involved in the processing of the web and are in contact with it, such as rolls, reels and various textures (wires, felts). The invention makes it possible to place the camera units or the like more freely and to select the imaging direction without complicating the interpretation of the measuring results because of the different imaging perspectives.

In an advantageous embodiment of the invention, the shrinkage of the fibre web in the transverse direction of the web is also taken into account, as the web travels from the wet end to the drier final section of the paper machine. When determining the transverse scale of the paper web and the coordinates system for the information measured by imaging, possible edge cutting of the web and possible lateral displacement of the web are also taken into account, if necessary.

By. taking into account the scale error included in the information measured by imaging and caused by the perspective, as well as the drying shrinkage of the fibre web in the transverse direction, edge cuttings and/or wandering of the web in the lateral direction, if necessary, it is possible to bring the information collected from different imaging or measuring positions into a format which is precisely uniform in the transverse scale. In difference to prior art, this also allows the automatical computer analysis of the measuring results in a significantly more efficient manner than before. Instead of a subjective analysis by the user, the invention makes it possible to use automatic pattern recognition and corresponding image processing techniques in the search for the cause of a given defect in the fibre web or a web break, in images recorded by successive camera units. This makes it faster and easier to recognize the cause of disturbances in the process and also makes it possible to collect statistical material relating to fault situations in a more reliable way than before.

The following, more detailed description of the invention with examples will more clearly illustrate, for anyone skilled in the art, preferred embodiments of the invention as well as advantages to be achieved with the invention in relation to background art.

BRIEF DESCRIPTION OF THE DRAWINGS

In the following, the invention will be described in more detail with reference to the appended drawings, in which.

DETAILED DESCRIPTION OF THE INVENTION

FIGS. 1 to 4 have been partly discussed already in connection with the description of prior art.

Figure 1:
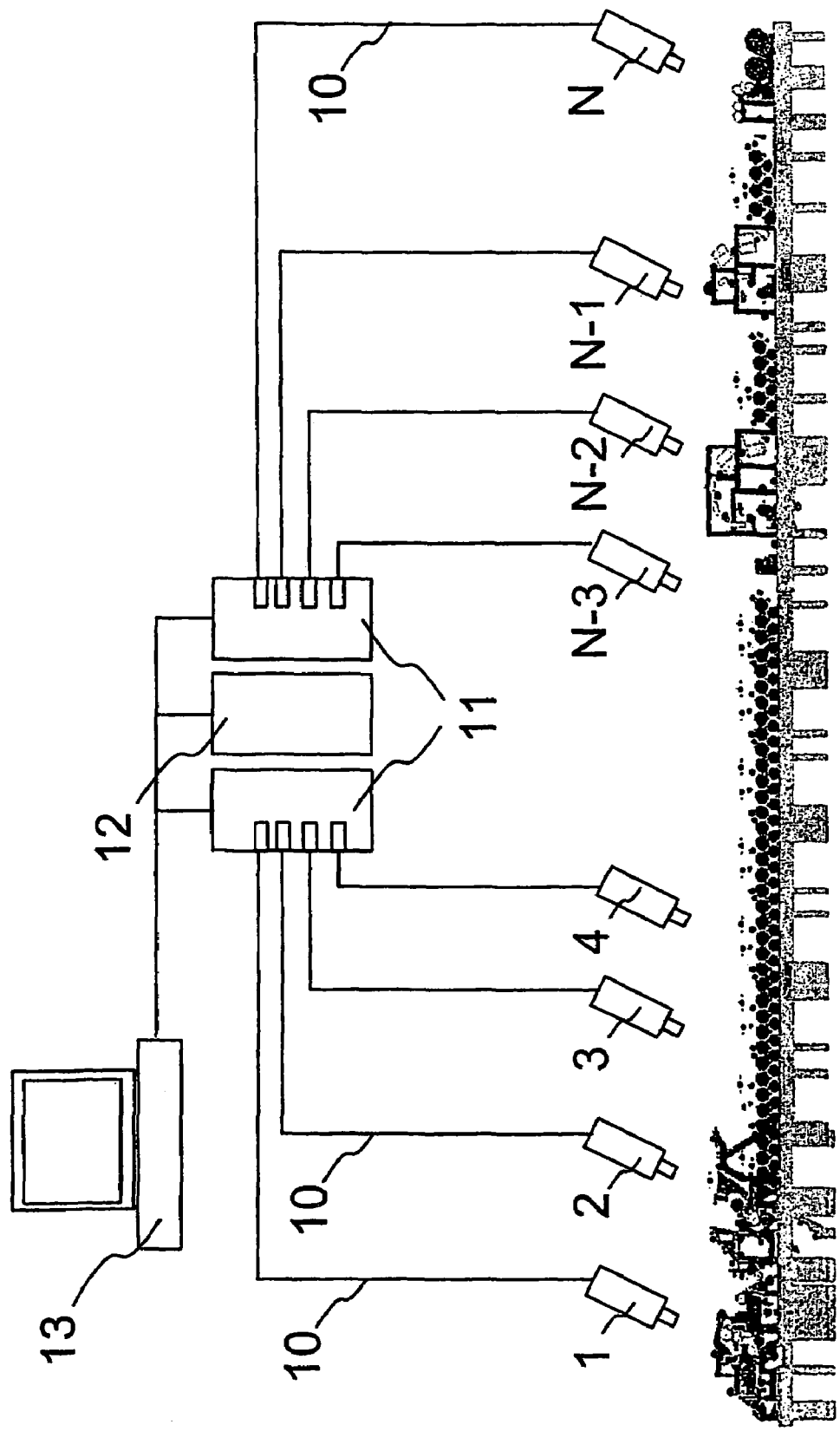
FIG. 1 shows the basic principle of the WRM system.
Figure 2:
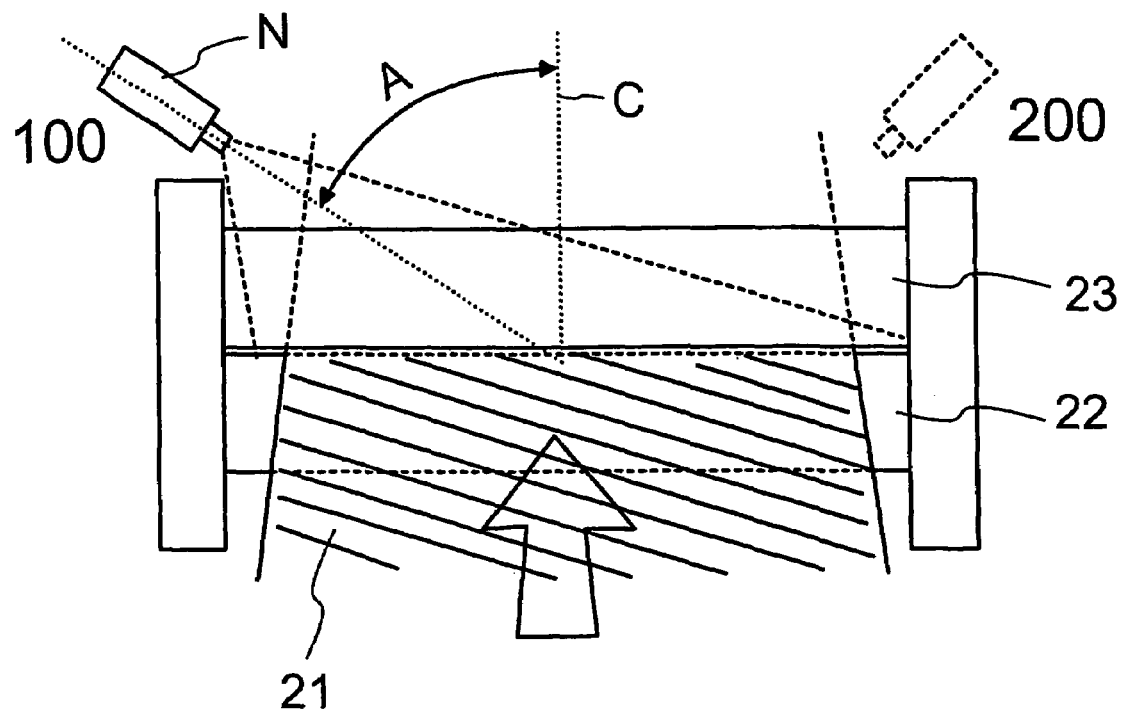
FIG. 2 shows, in a principle view, the placement of a single camera unit in a paper machine in the system of FIG. 1, seen in the travel direction of the web.
Figure 3:
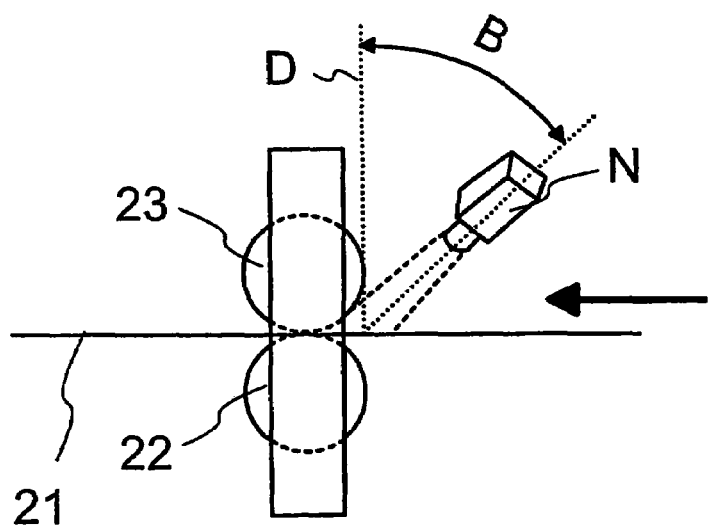
FIG. 3 shows the situation of FIG. 2, seen from the side of the paper machine.
Figure 4:
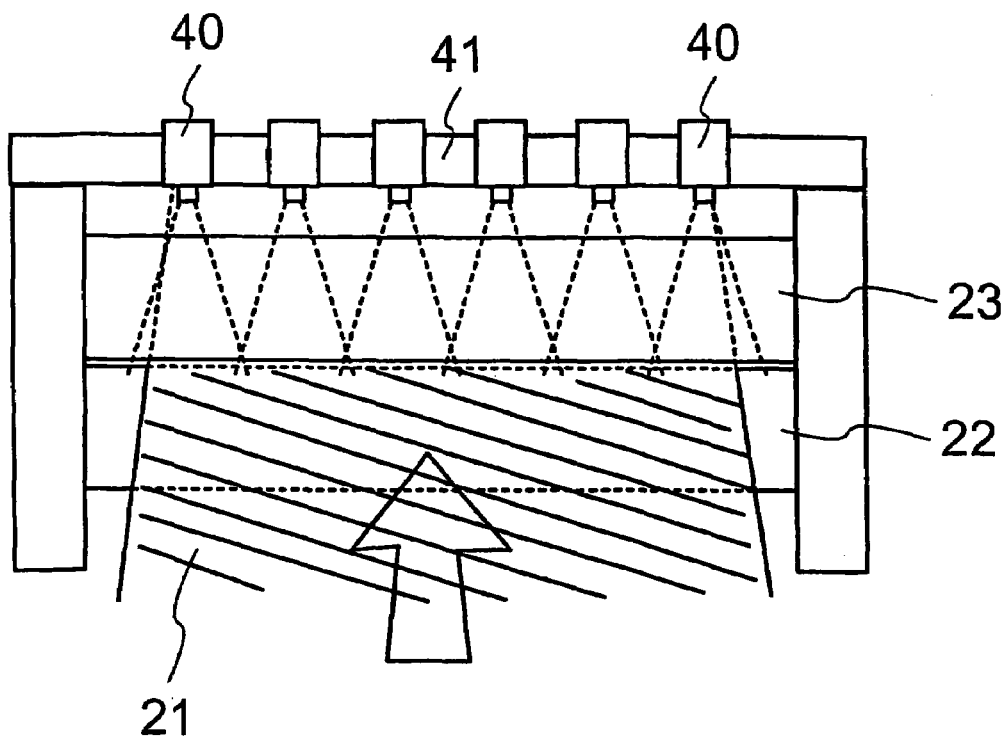
FIG. 4 shows the placement of camera units in a paper machine in the WIS system, in a way corresponding to that of FIG. 2.
Figure 5:
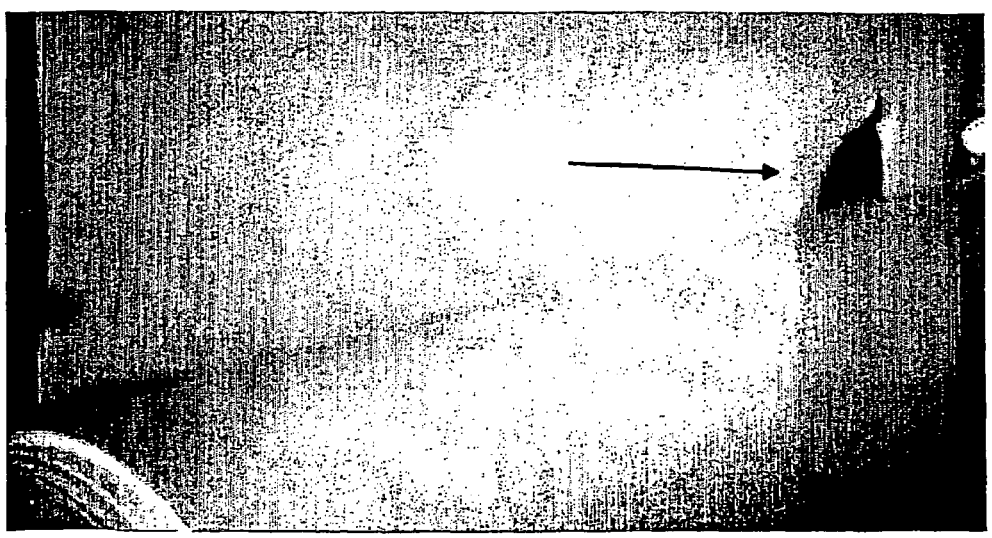
FIG. 5 shows, in a principle view, an example image recorded by a camera unit placed in connection with the press of a paper machine, according to FIGS. 2 and 3.
Figure 6:
FIG. 6 shows, in a principle view, an example image recorded by a camera unit placed in connection with the headbox of a paper machine, according to FIGS. 2 and 3.

With reference to FIGS. 5 and 6, we shall still briefly illustrate the effect of perspective caused by the imaging direction on the interpretation of the images.

FIG. 5 shows a typical image representing a fault situation and recorded by a CCD camera unit at the press of a paper machine. The placement of the camera unit in the imaging position corresponds, in principle, to the situation of FIGS. 2 and 3, in which the camera unit is placed, in relation to the paper web and the paper machine, outside the body of the paper machine, and is trained on the machine. FIG. 5 shows, at the point indicated with an arrow, a beginning web break.

Because of the directional error caused by the imaging perspective, it is very difficult to evaluate the distances in FIG. 5, particularly in the transverse direction of the paper web. Because of this, it is also impossible to determine the exact transverse location of the web break visible in the figure.

To find out the reason for the web break shown in FIG. 5, the camera images from the imaging positions preceding said imaging position must be analyzed, taking into account the speed of motion of the web in the machine direction, that is, the temporal synchronization of the camera units used in the different imaging positions. Without exact knowledge of the transverse location of the web break, this analysis is a process requiring accuracy and time, which, in systems of prior art, must currently be carried out primarily manually by the user.

To illustrate the problem, FIG. 6 shows an image from a camera unit placed in the imaging position preceding the imaging position of FIG. 5 in the travel direction of the web, after the headbox of the paper machine. FIG. 6 shows a fibre bundle, indicated with an arrow, which has been carried on the wire from the headbox of the paper machine and which will later cause an incipient web break of the fibre web detectable later in the press and shown in FIG. 5. To find the fibre bundle in the imaging position corresponding to FIG. 6, one must, in spite of the temporal synchronization of the images, scan through several successive images to find defects occurring at a given point in the transverse direction of the web. In the example of FIG. 6, the cause for the web break (fibre bundle) is very clearly visible, which facilitates the troubleshooting. However, in many cases, the disturbances causing a web break or a quality defect are not so clearly visible, which makes the analysis slower and more complicated.

Consequently, the analysis of a fault situation would be significantly facilitated if the troubleshooting could be focused precisely in a given area in the transverse direction of the paper web. To accelerate the analysis, the troubleshooting should also be carried out as automatically as possible, for example by utilizing digital image processing and pattern recognition. However, this requires that the different imaging perspectives of images recorded in different imaging positions are taken into account, which problem is solved by the present invention.

According to the invention, the imaging or observation area of each camera unit is calibrated when the camera unit is taken into use. Preferably, the calibration is performed so that when the camera unit has been fixed in its final position, calibration objects are arranged in the observation area of the camera unit, instead of or on the actual object to be imaged, the real distances between the calibration objects being precisely known. By means of a recorded calibration image of these calibration objects; it is possible to correct the scale distortion caused by the perspective of images recorded by the camera unit in the transverse direction of the paper web, wherein the real position of any image point can be determined in the images to be recorded later by the camera unit.

As the calibration objects, it is possible to use, for example, objects resembling a measuring tape or a table and placed physically in the imaging area. The calibration object can be, for example, a set square with scale marks representing both the transverse direction and the machine direction of the object. The calibration objects can also be various net-like or square-ruled objects with patterns or corresponding scale marks whose exact dimensions are known.

The calibration objects used can also be non-physical, for example light spots formed on the surface of the object by a laser beam or another type of structured light, or point matrices formed of such spots, or other lighting patterns used as scale marks. In this context, structured light refers to the projection of a light pattern, such as for example a light plane, a light matrix or another more complex light pattern on the surface of the object.

Scale marks included in or formed by the calibration object are used to determine the real distance represented by adjacent pixels in the calibration image. In this way, particularly in the transverse direction of the web, it is possible to determine the pixel resolution of the calibration as a function of the location, and further to determine the location in the transverse direction of the web, for example, as centimetres from one edge of the web. If it is necessary to perform the calibration all over again, for example, after a change in the location or position of the camera unit, the determination can be repeated in a very simple and fast manner.

In principle, the imaging or observation area of the camera unit can also be calibrated by measuring precisely the distances between the camera unit and the different parts of the object, as well as the imaging angles, wherein the perspective correction can be performed by computation. However, in practice, this is difficult to perform with a sufficient precision under industrial conditions.

Figure 7:
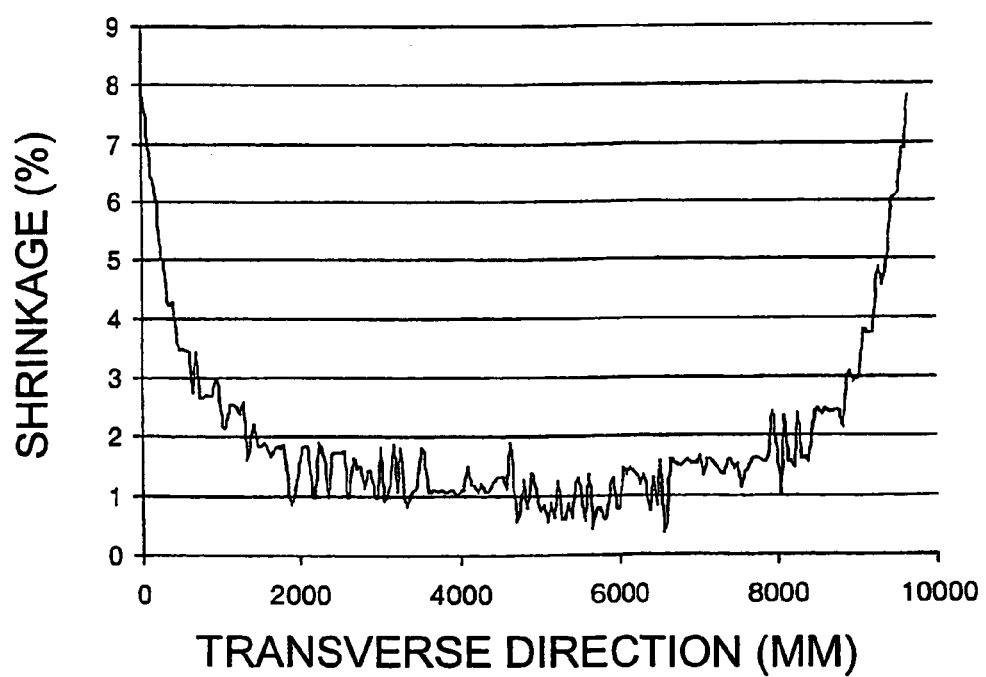
FIG. 7 shows an example of a typical transverse shrinkage profile of a fibre web, measured from a printing paper machine.

In an advantageous embodiment of the invention, when accommodating the scale in the transverse direction of the web, the shrinkage of the fibre web in the transverse direction is also taken into account, the moisture content being reduced when the web travels from the wet end to the terminal end of the paper machine. This shrinkage is typically higher at the edge areas of the web than in the middle area of the web. FIG. 7 shows a typical shrinkage profile of a fibre web in the transverse direction, measured in a printing paper machine. When the typical shrinkage profiles of the web corresponding to the different imaging positions are known, this information can be combined with the correction of the perspective error in the images. Thus, when an error is detected at a given location in the transverse direction of the web in a given imaging position, the precise location of this error in the transverse direction in the images can also be determined in the other imaging positions.

Information about the drying shrinkage of the web is needed when a given area of the web is compared in two different camera positions, if the fibre web has shrunk between these two positions because of drying. Thus, one must take into account that when the web is shrunk in the transverse direction, a given position of the web moves in a way corresponding to the shrinkage. When the non-linear model of the shrinkage is known (for example, the shrinkage profile shown in FIG. 7), it is possible to compute how much a given position of the web is transferred by the effect of the shrinkage in the transverse direction. When an image of the wet part is compared with an image of the dry part, for example the image of the dry part can be "spread" artificially according to the shrinkage pattern in the transverse direction to correspond to the position coordinates system of the wet part in the transverse direction.

According to the invention, the determination of the scale of the observation area in the transverse direction can be further specified by taking into account not only the drying shrinkage of the web but also the effect of edge cutting which the web is possibly subjected to. This is needed if the origin of the coordinates system in the imaging position under examination is bound to either one of the edges of the paper web. If, between two imaging positions, the fibre web is narrowed by cutting off an edge strip, this narrowing of the web caused by the cutting must be taken into account when determining the scale in the transverse direction of the web. In other words, at the latter imaging position, the edge of the web no longer corresponds to the origin of the coordinates system in the transverse direction, but the location of the edge of the web is determined according to the width of the cut-off edge strip.

Furthermore, the positioning of the observation area in the transverse direction can also be specified by taking into account the precise location of the web in the transverse direction, which may vary as the web, in practice, always wanders to some extent in the transverse direction. Typically, the web wanders some centimetres from one side to the other in the transverse direction. Thus, the precise transverse positioning requires that the position of the scale is not fixed; in other words, a given pixel in the images does not always represent the same location of the web in the transverse direction, but said whole scale "wanders" with the web in the transverse direction. Preferably, the correction is made in such a way that the images are first subjected to a perspective correction according to the invention, due to the imaging geometry, after which an image is available, in which the scale in the transverse direction corresponds to the real measuring scale at the imaging point. After this, the edges of the fibre web are separated from the image by means of an image analysis; in other words, the area covered by the fibre web (the location of the web) in the image is determined in the transverse direction. Next, the web area is spread by means of the edge cutting data and the shrinkage pattern to the same coordinates system as in the preceding imaging position, with which the image is to be compared. Finally, the image is focused precisely, if necessary, with the image from the preceding imaging position, one upon the other, taking into account the displacement of the web in the transverse direction, that is, the lateral wandering of the web.

In practice, the drying shrinkage is easier to take into account in the determination of the scale in the transverse direction of the web, because the drying shrinkage takes place primarily in a quite narrow area of dry substance in the drying section of the paper machine. In practice, it can thus be assumed without a great inaccuracy that substantially all of the drying shrinkage in the transverse direction takes place typically between two successive camera positions in the machine direction. Furthermore, the widths of the edge strips at their cutting points and the non-linear profile pattern of the drying shrinkage are normally available directly from the machine control and quality control system of the paper machine, because these data are needed for the adjustment of the quality control in the cross-machine direction of the paper machine. Similarly, the information on the position of the edge of the paper web (web width) is available from the control system of the paper machine, if it is not to be determined on the basis of the image analysis directly from the camera images. The present invention makes it possible to automate the analysis of measurement results in a computer in a significantly more effective way than before. Instead of or in addition to a subjective analysis by the user, the invention makes it possible to use automatic pattern recognition and corresponding image processing techniques in the search for the cause of a given defect in the fibre web or a web break, in images recorded by successive camera units. Thanks to the calibration of the scale in the transverse direction of the paper web, the information to be collected from different camera units can be brought to a format in which they can be compared with each other, wherein the images recorded by the different camera units can be used more easily to look for the same phenomenon in its different stages. Because a precise location in the transverse direction can now be determined for a detected phenomenon, information collected from fault situations can also be compiled into statistics in a more efficient way to control the operation of the paper machine.

By means of the invention, it is, for example, possible to use pattern recognition for the images to determine the precise location of a tear or a hole causing a web break (see FIG. 5), and to use said location data in the transverse direction to look for the actual cause of the web break in the image material of the preceding imaging positions (see FIG. 6). When the cause of the web break has been recognized either fully automatically or with the help of the user, the moment of time and the location of occurrence of the defect are compiled into statistics in the cross-machine and machine directions of the paper web. The statistics can be used for the evaluation of the condition of the different machine means of the paper machine, such as, for example, the drying felts. If the same machine means (i.e., the same location in the machine direction) and possibly even the same location in the transverse direction of the paper web continually turns out to be the cause of a web break, it is known that said machine means requires either maintenance or replacement.

Figure 8:
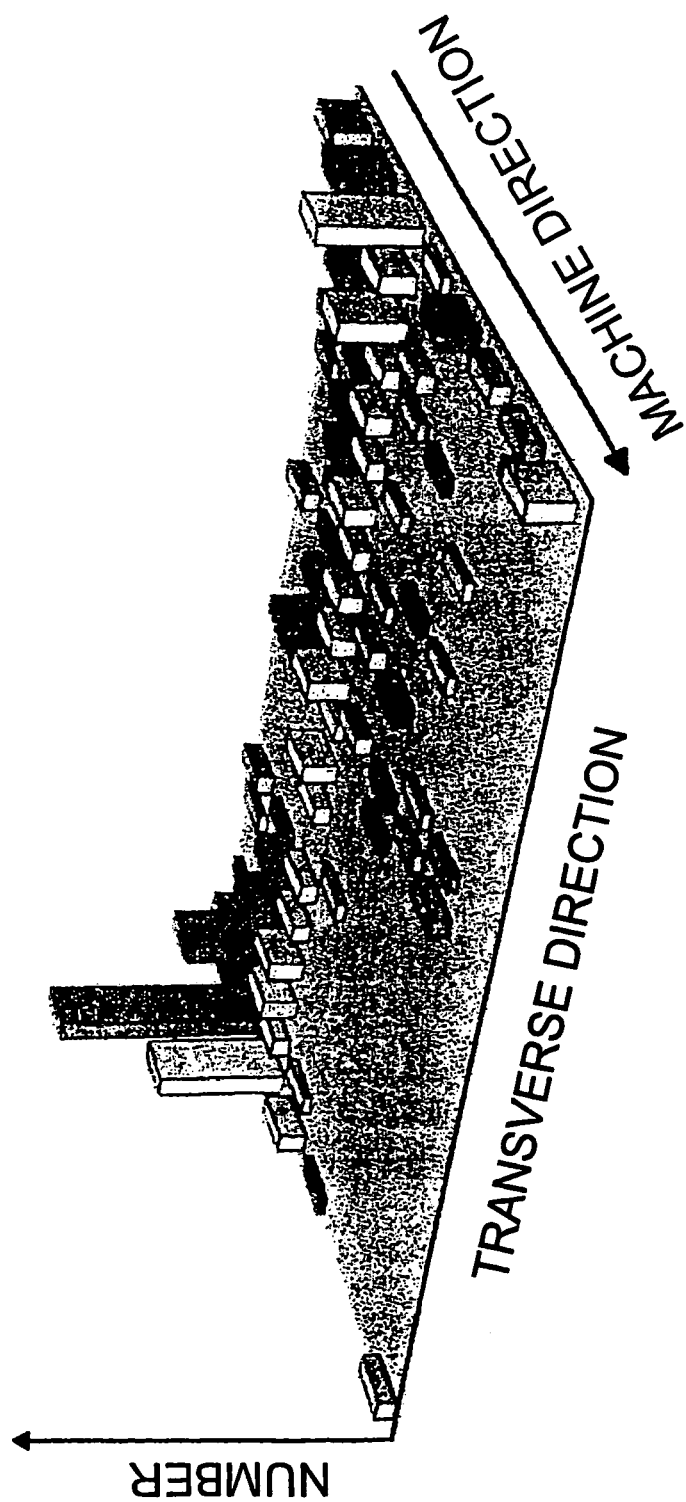
FIG. 8 shows an example of statistical information collected from a paper machine by using the invention.

FIG. 8 shows an example of statistical information to be collected from the paper machine by means of the invention. The information shown in the figure has been collected in eight different imaging positions in the machine direction of the web, at different steps in the process. The image material recorded in the different imaging positions has been brought into a format corresponding to each other in the transverse scale, and in each imaging position, events have been compiled into statistics by means of automatic image processing by dividing the width of the web into 21 separate observation areas. The vertical axis in FIG. 8 indicates the number of registered events. FIG. 8 shows clearly in which area in the transverse direction of the web the detected defects are accumulated in each imaging position. On the basis of this information, it will be obvious for a person skilled in the art to determine which machine means in the apparatus require control or maintenance.

It should be pointed out that in practice, statistics similar to FIG. 8 cannot be compiled manually without the present invention except for dividing the web to not more than a few separate observation areas in the transverse direction. The standardization of the scale in image material recorded by different camera units by means of the invention makes it possible to use efficient automatic image processing and pattern recognition methods in the statistical registration of events. Particularly in situations, in which the defect to be searched in the images is small in relation to the whole observation area of the image, it is possible to use, if necessary, the so-called ROI principle (ROI=Region of Interest) in the analyses. Thus, instead of examining the whole image area, the examination is only focused on a part of the image or observation area, for example on a given width of the web in the transverse direction. By means of the invention, images recorded in different imaging positions can now be used to determine the points corresponding to the same transverse area of the web, wherein the analysis of the images by utilizing automatic pattern recognition or with the help of the user becomes faster and more reliable. In digital image processing, the speed of the image processing is significantly affected by the size of the images to be processed. When utilizing the ROI principle, the image sizes to be processed become significantly smaller in their number of pixels, wherein it is also possible to use pattern recognition algorithms which are more complex and require more computing. The ROI principle is also advantageous in the analysis with the help of the user, because the user's full attention can thus be focused on a smaller area limited already in advance.

By means of the invention, the operation of the paper machine can, in some situations, be controlled by means of so-called focused analyses. In this way, one or more limited areas are defined for one camera unit in the transverse direction of the paper web, and the system automatically determines, by using the method of the invention, areas of corresponding sizes for all the other camera units in the transverse direction. Thanks to the calibration, the sections left inside said areas are precisely of the same width in the transverse direction of the paper web and correspond to the same transverse area of the paper web. After this, the system monitors disturbances or incontinuity phenomena in these one or more areas limited in the transverse direction, and records the corresponding images for further examination later. Focused analyses have the advantage that thanks to the smaller quantity of information to be stored in digital format, the images can be stored either entirely without compression of the images, or by using a smaller degree of compression. Thus, the image material to be stored remains of high quality, which makes it possible to use more precise analysis methods.

Using the method of the invention, the phenomena to be looked for in the paper web can be any phenomena different from the normal situation. As a reference, it is thus possible to use image material recorded of the normal state by averaging. As a reference, it is also possible to use stored image material of previously detected fault situations, wherein the system can be focused to look for defects of a given type, for example holes in the fibre web.

In addition to the optical monitoring of the fibre web itself, the method according to the invention can also be applied in the monitoring of various webs and rolls used in processes of manufacturing and/or finishing paper and/or board.

Using the method of the invention, it is possible to better detect and analyze such quick phenomena which cannot be appropriately detected by subjective analyses of prior art and primarily by the user, of image material or other corresponding location-specific measurement data. Thanks to the invention, the more effective statistical utilization of the measurement results helps to design maintenance and repair measures of production equipment better than before. In this way, unforeseen and extra stoppages are avoided. By various combinations of the methods and device structures presented in connection with the different embodiments of the invention presented above, it is possible to provide various embodiments of the invention which comply with the spirit of the invention. Therefore, the above-presented examples must not be interpreted to restrict the invention, but the embodiments of the invention can be freely varied within the scope of the inventive features presented in the claims hereinbelow.

Although the invention has been described above primarily in connection with camera systems recording a visual image, the invention is also suitable for the use of other kinds of optical measuring systems, in which location-specific information about an object is collected by imaging. The invention is thus suitable for use, for example, in connection with thermal cameras operating in the infrared range. Furthermore, the invention is also suitable for use in connection with other measuring devices based on imaging and spectral resolution, wherein the measurement result recorded by them includes, due to the imaging direction of the measuring devices, a distortion in the scale of the observation area, caused by the perspective. Such a measuring device may be, for example, an imaging spectrometer which comprises, for example, a grating spectrograph or a PGP type spectrograph (Prism-Grating-Prism) and a matrix detector coupled to the output of the spectrograph. In the imaging spectrometer, the spectrograph is arranged to record radiation of light focused on its elongated input aperture on a matrix detector in a spectrally resolved manner so that a location axis is formed on the matrix detector in the longitudinal direction of the input aperture, and a wavelength axis is formed on the matrix detector in a direction perpendicular to the longitudinal direction of the input aperture. The imaging spectrometer thus makes it possible to measure spectral information on the object in a location-specific manner in one direction. By using the method of the invention, the perspective error occurring in said direction can be compensated for.

The invention claimed is:

1. A method for controlling quality or a condition of a fibre web based on optical imaging diagnostics, comprising:
monitoring the fibre web under examination and/or a device that processes the fibre web in a running direction of the fibre web with several optical imaging measuring devices placed in successive measurement positions; and
calibrating scales of observation areas of the image measuring devices using one or more calibration objects placed in an observation area of the image measuring devices, to correct a perspective error caused by a position between the measuring devices and an object monitored by the measuring devices, wherein
the calibration scales of the observation areas of the imaging measuring devices are arranged to be comparable with each other.

2. The method according to claim 1, wherein during calibrating, the one or more calibration objects are arranged onto or in place of the fibre web and/or the device that processes the fibre web, in the observation area of the imaging measuring devices.

3. The method according to claim 2, wherein the one or more calibration objects are formed of single point objects, objects resembling a measuring tape or a table, and/or a net or square-ruled structures.

4. The method according to claim 2, wherein the one or more calibration objects are formed of a solid material.

5. The method according to claim 2, wherein the one or more calibration objects are formed of light points or lighting patterns reflected on the object.

6. The method according to claim 2, wherein a scale of an observation area of at least one imaging measuring device of the image measuring devices is calibrated in a transverse direction of the fibre web.

7. The method according to claim 1, wherein a scale of an observation area of at least one imaging measuring device of the image measuring devices is calibrated in a machine direction.

8. The method according to claim 1, wherein in different measuring positions, a drying shrinkage of the fibre web in a transverse direction and/or edge cutting of the fibre web and/or a displacement of the fibre web in the transverse direction are taken into account.

9. The method according to claim 1, wherein the imaging measuring devices used are cameras.

10. The method according to claim 9, wherein the cameras are cameras of a visible wavelength range or thermal cameras operating in an infrared range.

11. The method according to claim 1, wherein the imaging measuring devices used are imaging measuring devices based on spectral resolution.

12. The method according to claim 11, wherein the imaging measuring devices are imaging spectrometers.

13. The method according to claim 1, wherein information recorded in an imaging manner is produced substantially over a whole production width of the fibre web or on only a part of the production width of the fibre web.

14. The method according to claim 1, wherein information measured in an imaging manner and having a calibrated scale is subjected to automatic pattern recognition and/or image processing, to detect a defect or a phenomenon in the fibre web under examination and/or the device that processes the fibre web.

15. The method according to claim 1, wherein the device that processes the fibre web are wires, felts, rolls or reels.

* * * * *